United States Patent
Lurie

(10) Patent No.: US 10,835,175 B2
(45) Date of Patent: *Nov. 17, 2020

(54) END-TIDAL CARBON DIOXIDE AND AMPLITUDE SPECTRAL AREA AS NON-INVASIVE MARKERS OF CORONARY PERFUSION PRESSURE

(71) Applicant: ZOLL Medical Corporation, Chelmsford, MA (US)

(72) Inventor: Keith G. Lurie, Minneapolis, MN (US)

(73) Assignee: ZOLL Medical Corporation, Chelmsford, MA (US)

(*) Notice: Subject to any disclaimer, the term of this patent is extended or adjusted under 35 U.S.C. 154(b) by 241 days.

This patent is subject to a terminal disclaimer.

(21) Appl. No.: 15/927,607

(22) Filed: Mar. 21, 2018

(65) Prior Publication Data

US 2018/0206785 A1 Jul. 26, 2018

Related U.S. Application Data

(63) Continuation of application No. 15/420,653, filed on Jan. 31, 2017, now Pat. No. 9,949,686, which is a continuation of application No. 14/292,578, filed on May 30, 2014, now abandoned.

(60) Provisional application No. 61/829,176, filed on May 30, 2013.

(51) Int. Cl.
*A61B 5/00* (2006.01)
*A61N 1/39* (2006.01)
*A61H 31/00* (2006.01)
*A61B 5/0402* (2006.01)
*A61B 5/08* (2006.01)

(52) U.S. Cl.
CPC .......... *A61B 5/4836* (2013.01); *A61B 5/0402* (2013.01); *A61B 5/082* (2013.01); *A61B 5/74* (2013.01); *A61H 31/00* (2013.01); *A61H 31/005* (2013.01); *A61N 1/3987* (2013.01); *A61H 2230/206* (2013.01)

(58) Field of Classification Search
CPC .................................................. A61N 1/3987
USPC ............................................................ 607/6
See application file for complete search history.

(56) References Cited

U.S. PATENT DOCUMENTS

| | | | |
|---|---|---|---|
| 1,848,232 A | 3/1932 | Swope et al. |
| 2,325,049 A | 7/1943 | Frye et al. |
| 2,774,346 A | 12/1956 | Halliburton |
| 2,854,982 A | 10/1958 | Pagano |
| 2,904,898 A | 9/1959 | Marsden |
| 3,009,266 A | 11/1961 | Brook |

(Continued)

FOREIGN PATENT DOCUMENTS

| | | |
|---|---|---|
| AU | 1487792 B | 10/1992 |
| AU | 60539 B | 11/1994 |

(Continued)

OTHER PUBLICATIONS

US 5,584,866 A, 12/1996, Kroll et al. (withdrawn)

(Continued)

*Primary Examiner* — Nadia A Mahmood
(74) *Attorney, Agent, or Firm* — The Webb Law Firm

(57) ABSTRACT

End-tidal carbon dioxide ($ETCO_2$) measurements may be used alone as a guide to determine when to defibrillate an individual. Alternatively, $ETCO_2$ measurements may be used in combination with amplitude spectral area measurements as a guide to determine when to defibrillate an individual.

20 Claims, 8 Drawing Sheets

(56) References Cited

U.S. PATENT DOCUMENTS

| | | |
|---|---|---|
| 3,049,811 A | 8/1962 | Ruben |
| 3,068,590 A | 12/1962 | Padellford |
| 3,077,884 A | 2/1963 | Batrow et al. |
| 3,191,596 A | 6/1965 | Bird et al. |
| 3,199,225 A | 8/1965 | Robertson et al. |
| 3,209,469 A | 10/1965 | James |
| 3,216,413 A | 11/1965 | Arecheta Mota |
| 3,274,705 A | 9/1966 | Breakspear |
| 3,276,147 A | 10/1966 | Padellford |
| 3,307,541 A | 3/1967 | Hewson |
| 3,357,426 A | 12/1967 | Cohen |
| 3,420,232 A | 1/1969 | Bickford |
| 3,459,216 A | 8/1969 | Bloom et al. |
| 3,467,092 A | 9/1969 | Bird et al. |
| 3,509,899 A | 5/1970 | Hewson |
| 3,515,163 A | 6/1970 | Freeman |
| 3,523,529 A | 8/1970 | Kissen |
| 3,552,390 A | 1/1971 | Muller |
| 3,562,924 A | 2/1971 | Baerman et al. |
| 3,562,925 A | 2/1971 | Baermann et al. |
| 3,568,333 A | 3/1971 | Clark |
| 3,662,751 A | 5/1972 | Barkalow et al. |
| 3,669,108 A | 6/1972 | Sundblom et al. |
| 3,734,100 A | 5/1973 | Walker et al. |
| 3,739,776 A | 6/1973 | Bird et al. |
| 3,794,043 A | 2/1974 | McGinnis |
| 3,815,606 A | 6/1974 | Mazal |
| 3,834,383 A | 9/1974 | Weigl et al. |
| 3,872,609 A | 3/1975 | Smrcka |
| 3,874,093 A | 4/1975 | Garbe |
| 3,875,626 A | 4/1975 | Tysk et al. |
| 3,933,171 A | 1/1976 | Hay |
| 3,949,388 A | 4/1976 | Fuller |
| 3,973,564 A | 8/1976 | Carden |
| 3,981,398 A | 9/1976 | Boshoff |
| 3,993,059 A | 11/1976 | Sjostrand |
| 4,037,595 A | 7/1977 | Elam |
| 4,041,943 A | 8/1977 | Miller |
| 4,054,134 A | 10/1977 | Kritzer |
| 4,077,400 A | 3/1978 | Harrigan |
| 4,077,404 A | 3/1978 | Elam |
| 4,095,590 A | 6/1978 | Harrigan |
| 4,166,458 A | 9/1979 | Harrigan |
| 4,193,406 A | 3/1980 | Jinotti |
| 4,198,963 A | 4/1980 | Barkalow et al. |
| 4,226,233 A | 10/1980 | Kritzer |
| 4,237,872 A | 12/1980 | Harrigan |
| 4,240,419 A | 12/1980 | Furlong et al. |
| 4,259,951 A | 4/1981 | Chernack et al. |
| 4,262,667 A | 4/1981 | Grant |
| 4,297,999 A | 11/1981 | Kitrell |
| 4,298,023 A | 11/1981 | McGinnis |
| 4,316,458 A | 2/1982 | Hammerton-Fraser |
| 4,320,754 A | 3/1982 | Watson et al. |
| 4,326,507 A | 4/1982 | Barkalow |
| 4,331,426 A | 5/1982 | Sweeney |
| 4,349,015 A | 9/1982 | Alferness |
| 4,360,345 A | 11/1982 | Hon |
| 4,397,306 A | 8/1983 | Weisfeldt et al. |
| 4,424,806 A | 1/1984 | Newman et al. |
| 4,446,864 A | 5/1984 | Watson et al. |
| 4,448,192 A | 5/1984 | Stawitcke et al. |
| 4,449,526 A | 5/1984 | Elam |
| 4,481,938 A | 11/1984 | Lindley |
| 4,501,582 A | 2/1985 | Schulz |
| 4,513,737 A | 4/1985 | Mabuchi |
| 4,519,388 A | 5/1985 | Schwanbom et al. |
| 4,520,811 A | 6/1985 | White et al. |
| 4,533,137 A | 8/1985 | Sonne |
| 4,543,951 A | 10/1985 | Phuc |
| 4,588,383 A | 5/1986 | Parker et al. |
| 4,598,706 A | 7/1986 | Darowski et al. |
| 4,601,465 A | 7/1986 | Roy |
| 4,602,653 A | 7/1986 | Ruiz-Vela et al. |
| 4,637,386 A | 1/1987 | Baum |
| 4,738,249 A | 4/1988 | Linman et al. |
| 4,750,493 A | 6/1988 | Brader |
| 4,774,941 A | 10/1988 | Cook |
| 4,797,104 A | 1/1989 | Laerdal et al. |
| 4,807,638 A | 2/1989 | Sramek |
| 4,809,683 A | 3/1989 | Hanson |
| 4,827,935 A | 5/1989 | Geddes et al. |
| 4,828,501 A | 5/1989 | Ingenito et al. |
| 4,863,385 A | 9/1989 | Pierce |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,150,291 A | 9/1992 | Cummings et al. |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |
| 5,295,481 A | 3/1994 | Geeham |
| 5,301,667 A | 4/1994 | McGrail et al. |
| 5,305,743 A | 4/1994 | Brain |
| 5,306,293 A | 4/1994 | Zacouto |
| 5,312,259 A | 5/1994 | Flynn |
| 5,313,938 A | 5/1994 | Garfield et al. |
| 5,316,907 A | 5/1994 | Lurie et al. |
| 5,330,514 A | 7/1994 | Egelandsdal et al. |
| 5,335,654 A | 8/1994 | Rapoport |
| 5,353,788 A | 10/1994 | Miles |
| 5,355,879 A | 10/1994 | Brain |
| 5,359,998 A | 11/1994 | Lloyd |
| 5,366,231 A | 11/1994 | Hung |
| 5,377,671 A | 1/1995 | Biondi et al. |
| 5,383,786 A | 1/1995 | Kohnke |
| 5,385,547 A | 1/1995 | Wong et al. |
| 5,388,575 A | 2/1995 | Taube |
| 5,392,774 A | 2/1995 | Sato |
| 5,395,399 A | 3/1995 | Rosenwald |
| 5,397,237 A | 3/1995 | Dhont et al. |
| 5,398,714 A | 3/1995 | Price |
| 5,413,110 A | 5/1995 | Cummings et al. |
| 5,423,685 A | 6/1995 | Adamson et al. |
| 5,423,772 A | 6/1995 | Lurie et al. |
| 5,425,742 A | 6/1995 | Joy |
| 5,437,272 A | 8/1995 | Fuhrman |
| 5,452,715 A | 9/1995 | Boussignac |
| 5,454,779 A | 10/1995 | Lurie et al. |
| 5,458,562 A | 10/1995 | Cooper |
| 5,468,151 A | 11/1995 | Egelandsdal et al. |
| 5,474,533 A | 12/1995 | Ward et al. |
| 5,477,860 A | 12/1995 | Essen-Moller |
| 5,490,820 A | 2/1996 | Schock et al. |
| 5,492,115 A | 2/1996 | Abramov et al. |
| 5,492,116 A | 2/1996 | Scarberry et al. |
| 5,496,257 A | 3/1996 | Kelly |
| 5,517,986 A | 5/1996 | Starr et al. |

(56) References Cited

U.S. PATENT DOCUMENTS

| | | |
|---|---|---|
| 5,544,648 A | 8/1996 | Fischer, Jr. |
| 5,549,106 A | 8/1996 | Gruenke et al. |
| 5,549,581 A | 8/1996 | Lurie et al. |
| 5,551,420 A | 9/1996 | Lurie et al. |
| 5,557,049 A | 9/1996 | Ratner |
| 5,580,255 A | 12/1996 | Flynn |
| 5,582,182 A | 12/1996 | Hillsman |
| 5,588,422 A | 12/1996 | Lurie et al. |
| 5,593,306 A | 1/1997 | Kohnke |
| 5,614,490 A | 3/1997 | Przybelski |
| 5,617,844 A | 4/1997 | King |
| 5,618,665 A | 4/1997 | Lurie et al. |
| 5,619,665 A | 4/1997 | Emma |
| 5,628,305 A | 5/1997 | Melker |
| 5,632,298 A | 5/1997 | Artinian |
| 5,643,231 A | 7/1997 | Lurie et al. |
| 5,645,522 A | 7/1997 | Lurie et al. |
| 5,657,751 A | 8/1997 | Karr, Jr. |
| 5,678,535 A | 10/1997 | DiMarco |
| 5,685,298 A | 11/1997 | Idris |
| 5,692,498 A | 12/1997 | Lurie et al. |
| 5,697,364 A | 12/1997 | Chua et al. |
| 5,701,883 A | 12/1997 | Hete et al. |
| 5,701,889 A | 12/1997 | Danon |
| 5,704,346 A | 1/1998 | Inoue |
| 5,720,282 A | 2/1998 | Wright |
| 5,722,963 A | 3/1998 | Lurie et al. |
| 5,730,122 A | 3/1998 | Lurie |
| 5,735,876 A | 4/1998 | Kroll et al. |
| 5,738,637 A | 4/1998 | Kelly et al. |
| 5,743,864 A | 4/1998 | Baldwin, II |
| 5,782,883 A | 7/1998 | Kroll et al. |
| 5,794,615 A | 8/1998 | Estes |
| 5,806,512 A | 9/1998 | Abramov et al. |
| 5,814,086 A | 9/1998 | Hirschberg et al. |
| 5,817,997 A | 10/1998 | Wernig |
| 5,823,185 A | 10/1998 | Chang |
| 5,823,787 A | 10/1998 | Gonzalez et al. |
| 5,827,893 A | 10/1998 | Lurie et al. |
| 5,832,920 A | 11/1998 | Field |
| 5,853,292 A | 12/1998 | Eggert et al. |
| 5,881,725 A | 3/1999 | Hoffman et al. |
| 5,885,084 A | 3/1999 | Pastrick et al. |
| 5,891,062 A | 4/1999 | Schock et al. |
| 5,896,857 A | 4/1999 | Hely et al. |
| 5,916,165 A | 6/1999 | Duchon et al. |
| 5,919,210 A | 7/1999 | Lurie et al. |
| 5,927,273 A | 7/1999 | Federowicz et al. |
| 5,937,853 A | 8/1999 | Strom |
| 5,941,710 A | 8/1999 | Lampotang et al. |
| 5,975,081 A | 11/1999 | Hood et al. |
| 5,977,091 A | 11/1999 | Nieman et al. |
| 5,984,909 A | 11/1999 | Lurie et al. |
| 5,988,166 A | 11/1999 | Hayek |
| 6,001,085 A | 12/1999 | Lurie et al. |
| 6,010,470 A | 1/2000 | Albery et al. |
| 6,029,667 A | 2/2000 | Lurie |
| 6,042,532 A | 3/2000 | Freed et al. |
| 6,062,219 A | 5/2000 | Lurie et al. |
| 6,078,834 A | 6/2000 | Lurie et al. |
| 6,086,582 A | 7/2000 | Altman et al. |
| 6,123,074 A | 9/2000 | Hete et al. |
| 6,131,571 A | 10/2000 | Lampotang et al. |
| 6,155,257 A | 12/2000 | Lurie et al. |
| 6,155,647 A | 12/2000 | Albecker, III |
| 6,165,105 A | 12/2000 | Boutellier et al. |
| 6,167,879 B1 | 1/2001 | Sievers et al. |
| 6,174,295 B1 | 1/2001 | Cantrell et al. |
| 6,176,237 B1 | 1/2001 | Wunderlich et al. |
| 6,193,519 B1 | 2/2001 | Eggert et al. |
| 6,209,540 B1 | 4/2001 | Sugiura et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie et al. |
| 6,296,490 B1 | 10/2001 | Bowden |
| 6,312,399 B1 | 11/2001 | Lurie et al. |
| 6,334,441 B1 | 1/2002 | Zowtiak et al. |
| 6,356,785 B1 | 3/2002 | Snyder et al. |
| 6,369,114 B1 | 4/2002 | Weil et al. |
| 6,374,827 B1 | 4/2002 | Bowden et al. |
| 6,390,996 B1 | 5/2002 | Halperin et al. |
| 6,425,393 B1 | 7/2002 | Lurie et al. |
| 6,439,228 B1 | 8/2002 | Hete et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,970 B2 | 3/2003 | DeVries et al. |
| 6,526,973 B1 | 3/2003 | Lurie et al. |
| 6,536,432 B2 | 3/2003 | Truschel |
| 6,544,172 B2 | 4/2003 | Toeppen-Sprigg |
| 6,555,057 B1 | 4/2003 | Barbut et al. |
| 6,578,574 B1 | 6/2003 | Kohnke |
| 6,584,973 B1 | 7/2003 | Biondi et al. |
| 6,587,726 B2 | 7/2003 | Lurie et al. |
| 6,595,213 B2 | 7/2003 | Bennarsten |
| 6,604,523 B2 | 8/2003 | Lurie et al. |
| 6,622,274 B1 | 9/2003 | Lee et al. |
| 6,622,724 B1 | 9/2003 | Truitt et al. |
| 6,631,716 B1 | 10/2003 | Robinson et al. |
| 6,656,166 B2 | 12/2003 | Lurie et al. |
| 6,662,032 B1 | 12/2003 | Gavish et al. |
| 6,676,613 B2 | 1/2004 | Cantrell et al. |
| 6,726,634 B2 | 4/2004 | Freeman |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,860,265 B1 | 3/2005 | Emerson |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie et al. |
| 7,066,173 B2 | 6/2006 | Banner et al. |
| 7,082,945 B2 | 8/2006 | Lurie |
| 7,096,866 B2 | 8/2006 | Be'eri et al. |
| 7,174,891 B2 | 2/2007 | Lurie et al. |
| 7,185,649 B2 | 3/2007 | Lurie |
| 7,188,622 B2 | 3/2007 | Martin et al. |
| 7,195,012 B2 | 3/2007 | Lurie |
| 7,195,013 B2 | 3/2007 | Lurie |
| 7,204,251 B2 | 4/2007 | Lurie |
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie |
| 7,469,700 B2 | 12/2008 | Baran |
| 7,487,773 B2 | 2/2009 | Li |
| 7,500,481 B2 | 3/2009 | Delache et al. |
| 7,571,725 B2 | 8/2009 | Wickham et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,882,703 B2 | 11/2014 | Hickle |

(56) References Cited

U.S. PATENT DOCUMENTS

| | | |
|---|---|---|
| 8,939,922 B2 | 1/2015 | Strand et al. |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0037784 A1 | 2/2003 | Lurie |
| 2003/0062040 A1 | 4/2003 | Lurie et al. |
| 2003/0062041 A1 | 4/2003 | Keith et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt et al. |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0199566 A1 | 8/2007 | Be'eri |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1 | 1/2009 | Metzger et al. |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0179442 A1 | 7/2010 | Lurie |
| 2010/0319691 A1 | 12/2010 | Lurie et al. |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0197887 A1 | 8/2011 | Truschel et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1 | 5/2013 | Robitaille et al. |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |
| 2015/0352302 A1 | 12/2015 | Kuypers et al. |

FOREIGN PATENT DOCUMENTS

| | | |
|---|---|---|
| AU | 687942 B2 | 5/1995 |
| CA | 668771 A | 8/1963 |
| CA | 2077608 A1 | 3/1993 |
| CA | 2214887 A1 | 9/1996 |
| CN | 1183731 A | 6/1998 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0509773 A1 | 10/1992 |
| EP | 0560440 A1 | 9/1993 |
| EP | 0623033 A1 | 11/1994 |
| GB | 1344862 A | 1/1974 |
| GB | 1465127 A | 2/1977 |
| GB | 2117250 A | 10/1983 |
| GB | 2139099 A | 11/1984 |
| JP | 2005675 A | 1/2005 |
| JP | 2006524543 A | 11/2006 |
| JP | 2007504859 A | 3/2007 |
| WO | 905518 A1 | 5/1990 |
| WO | 9302439 A1 | 2/1993 |
| WO | 9321982 A1 | 11/1993 |
| WO | 9426229 A1 | 11/1994 |
| WO | 9513108 A1 | 5/1995 |
| WO | 9528193 A1 | 10/1995 |
| WO | 9628215 A1 | 9/1996 |
| WO | 9820938 A1 | 5/1998 |
| WO | 9947197 A1 | 9/1999 |
| WO | 9963926 A2 | 12/1999 |
| WO | 0020061 A1 | 4/2000 |
| WO | 0102049 A2 | 1/2001 |
| WO | 0170092 A2 | 9/2001 |
| WO | 0170332 A2 | 9/2001 |
| WO | 02092169 A1 | 11/2002 |
| WO | 2004096109 A3 | 11/2004 |
| WO | 2006088373 A1 | 8/2006 |
| WO | 2008147229 A1 | 12/2008 |
| WO | 2010044034 A1 | 4/2010 |
| WO | 2013064888 A1 | 5/2013 |
| WO | 2013096495 A1 | 6/2013 |
| WO | 2014026193 A1 | 2/2014 |

OTHER PUBLICATIONS

Yannopoulos et al., "Controlled pauses at the initiation of sodium nitroprussdi e-enhanced cardiopulmonary resuscitation facilitate neurological and cardiac recovery after 15 minutes of untreated ventricular fibrillation," Critical Care Medicine, 2012, pp. 1-8, vol. 40:5.

Zhao et. al., "Inhibition of myocardial injury by ischemic postconditioning during reperfusion: comparison with ischemic preconditioning," AJP Heart Circ Physiol, 2003, pp. H579-H588, vol. 285.

Zoll Autopulse Non-Invasive Cardiac Support Pump, obtained online on 715106 at http://www.zoll.com/product.aspx?id=84,1 page.

Advanced Circulatory Systems, Inc. (2005). Introducing ResQPOD® (#49-0324-000, 01) [Brochure]. Roseville, MN: Advanced Circulatory Systems, Inc., 2 pages.

Advanced Circulatory Systems, Inc. (2006). ResQPOD® Circulatory Enhancer: Strengthening the Chain of Survival (#49-0336-000, 02). [Brochure]. Roseville.MN: Advanced Circulatory Systems, Inc., 2 pages.

Advanced Circulatory Systems, Inc. (2006). ResQPOD® Circulatory Enhancer: Strengthening the Chain of Survival (#49-0336-000, 01) [Brochure]. Roseville, MN: Advanced Circulatory Systems, Inc. 2 pages.

Advanced Circulatory Systems, Inc. (2009). ResQPOD® Perfusion on Demand: ResQPOD Impedance Threshold Device (#49-0324-001, 02) [Brochure]. Roseville, MN: Advanced Circulatory Systems, Inc., 2 pages.

(56) References Cited

OTHER PUBLICATIONS

Advanced Circulatory Systems, Inc. (2010), ResQPOD Impedance Threshold Device: Strengthening the Chain of Survival (#49-0336000, 05) [Brochure], Roseville, MN: Advanced Circulatory Systems, Inc. 2 pages.
Advanced Circulatory Systems, Inc. (2010), ResQPOD Impedance Threshold Device: Strengthening the Chain of Survival (#49-0336000, 04) [Brochure], Roseville, MN: Advanced Circulatory Systems, Inc. 2 pages.
Advanced Circulatory Systems, Inc. (2010), ResQPOD Impedance Threshold Device 10.0: Strengthening the Chain of Survival (#49-0336000, 03) [Brochure], Roseville, MN: Advanced Circulatory Systems, Inc. 2 pages.
Advanced Circulatory Systems, Inc. (2010). ResQPOD® Perfusion on Demand: ResQPOD Impedance Threshold Device (#49-0324-001, 03) [Brochure]. Roseville, MN: Advanced Circulatory Systems, Inc., 2 pages.
Advanced Circulatory Systems, Inc. (2011). ResQPOD® Perfusion on Demand: ResQPOD Impedance Threshold Device (#49-0324-001, 04) [Brochure]. Roseville, MN: Advanced Circulatory Systems, Inc. 2 pages.
Advanced Circulatory Systems. Inc. (2011). ResQPOD® Perfusion on Demand: ResQPOD Impedance Threshold Device (#49-0324-001, 05) [Brochure]. Roseville, MN: Advanced Circulatory Systems, Inc., 2 pages.
Advanced Circulatory Systems, Inc. (2011), ResQPOD ITD: Strengthening the Chain of Survival (#49-0336000, 06) [Brochure], Roseville, MN: Advanced Circulatory Systems, Inc. 2 pages.
Advanced Circulatory Systems, Inc. (Aug. 2011), Early Intervention is Life-Saving in Cardiac Arrest (#49-0864-000,01) [Brochure], Roseville, MN: Advanced Circulatory Systems, Inc. 2 pages.
Advanced Circulatory Systems, Inc. (Aug. 2011), Early Intervention is Life-Saving in Cardiac Arrest (#49-0864-000,02) [Brochure], Roseville, MN: Advanced Circulatory Systems, Inc. 2 pages.
Advanced Circulatory Systems, Inc. (Jan. 2012), Benefits of the ResQPOD Based Upon the ROC Primed Study (#49-0864-000,03) [Brochure], Roseville, MN: Advanced Circulatory Systems, Inc. 2 pages.
Advanced Circulatory Systems, Inc. (Mar. 2012), Benefits of the ResQPOD Based Upon the ROC Primed Study (#49-0864-000,04) [Brochure], Roseville, MN: Advanced Circulatory Systems, Inc. 2 pages.
Advanced Circulatory Systems, Inc. (2013), ResQPOD More than a Heartbeat (#49-0336-000,08) [Brochure], Roseville, MN: Advanced Circulatory Systems, Inc. 2 pages.
Advanced Circulatory Systems, Inc. (Jan. 2013), Emerging Data: The Resuscitation Outcomes Consortium (ROC) Primed Study on the Efficacy of the ITD (#49-0864-000,05) [Brochure], Roseville, MN: Advanced Circulatory Systems, Inc. 2 pages.
Advanced Circulatory Systems, Inc. (Jan. 2014), Emerging Data: The Resuscitation Outcomes Consortium (ROC) Primed Study on the Efficacy of the ITD (#49-0864-000,06) [Brochure], Roseville, MN: Advanced Circulatory Systems, Inc. 2 pages.
Ambu InternationalNS Directions for use of Ambu® CardioPump™ —Sep. 1992, 8 pages.
Aufderheide et al., "Hyperventilation-Induced Hypotension During Cardiopulmonary Resuscitation," Circulation; 2004, pp. 1960-1965, vol. 109:16.
Aufderheide et al., "Standard cardiopulmonary resuscitation versus active compression-decompression cardiopulmonary resuscitation with augmentation of negative intrathoracic pressure for out-of-hospital cardiac arrest: A randomized trial", 2011, Lancet, pp. 301-311, vol. 377.
Azim et al. "The use of bispectral index during a cardiopulmonary arrest: a potential predictor of cerebral perfusion," Anaesthesia, 2004, pp. 610-612, vol. 59.
Babbs, "CPR Techniques that Combine Chest and Abdominal Compression and Decompression: Hemodynamic Insights from a Spreadsheet Model," Circulation, 1999, pp. 2146-2152.

Christenson et al., "Abdominal Compressions During CPR: Hemodynamic Effects of Altering Timing and Force", The Journal of Emergency Medicine, 1992, pp. 257-266, vol. 10, pp. 257-266.
Cohen et al., "Active compression-decompression resuscitation: A novel method of cardiopulmonary resuscitation," American Heart Journal, pp. 1145-1150, vol. 124:5.
Cohen et al., "Active Compression-Decompression: A New Method of Cardiopulmonary Resuscitation," 1992, JAMA, pp. 2916-2923, vol. 267:29.
Dupuis, "Ventilators—Theory and Clinical Application," Jan. 1986, The C.V. Mosby Company, pp. 447-448.
Geddes et al., "Electrically Produced Artificial Ventilation," Medical Instrumentation, 1988, pp. 263-271, vol. 22:5.
Geddes et al., "Optimum Stimulus Frequency for Contracting the Inspiratory Muscles with Chest-Surface Electrodes to Produce Artificial respiration," Annals of Biomedical Engineering, 1990, pp. 103-108, vol. 18.
Geddes et al., "Inspiration Produced by Bilateral Electromagnetic, Cervical Phrenic Nerve Stimulation in Man," IEEE Transactions on Biomedical Engineering, 1991, pp. 1047-1048, vol. 38:9.
Geddes, "Electroventilation—A Missed Opportunity?" Biomedical Instrumentation & Technology, 1998, pp. 401-414.
Glenn et al., "Diaphragm Pacing by Electrical Stimulation of the Phrenic Nerve," Neurosurgery, 1985, pp. 974-984, vol. 17:6.
Glenn et al., "Twenty Years of Experience in Phrenic Nerve Stimulation to Pace the Diaphragm," Nov./Dec. 1986, Part I, Pace 9, pp. 780-784.
Guidelines for Cardiopulmonary Resuscitation and Emergency Cardiac Care, JAMA, 1992, pp. 2172-2177, vol. 268.
Johnson et al. "Time to throw away your stethoscope? Capnography: Evidence-based patient monitoring technology," J. Radio. Nurs., 2011, pp. 25-34, vol. 30.
Jung et al., "Usefulness of the bispectral index during cardiopulmonary resuscitation," Korean J Anesthesiol, 2013, pp. 69-72, vol. 64:1.
Kotze et al., "Diaphragm pacing in the treatment of ventilatory failure," SAMT, 1995, pp. 223-224, vol. 68.
Laghi et al., "Comparison of Magnetic and Electrical Phrenic Nerve Stimulation in assessment of Diaphragmatic Contractility," American Physiological Society, 1996, pp. 1731-1742.
Lindner et al., "Effects of Active Compression-Decompression Resuscitation on Myocardia land Cerebral Blood Flow in Pigs," Circulation, 1993, pp. 1254-1263, vol. 88:3.
Lurie et al., "Regulated to Death: The Matter of Informed Consent for Human Experimentation in Emergency Resuscitation Research," PACE, 1995, pp. 1443-1447, vol. 8.
Lurie et al., "Comparison of a 10-Breaths-Per-Minute Versus a 2-Breaths -Per-Minute Strategy During Cardiopulmonary Resuscitation in a Porcine Model of Cardiac Arrest," Respiratory Care, 2008, pp. 862-870, vol. 53:7.
Michigan Instruments, Inc., Thumper 1007CC Continuous Compression Cardiopulmonary Resuscitation System, obtained online Jul. 15, 2006 at http://www.michiganinstruments.com/resus-thumper. htm, 1 page.
Mushin et al., "Automatic Ventilation of the Lungs—The Lewis-Leigh Inflating Valve," 1969, Blackwell Scientific, Oxford, GB, p. 838.
Schultz et al., "Sodium nitroprusside enhanced cardiopulmonary resuscitation (SNPeCPR) improves vital organ perfusion pressures and carotid blood flow in a porcine model of cardiac arrest," Resuscitation, 2012, pp. 374-377, vol. 83.
Segal et al., "Ischemic postconditioning at the initiation of cardiopulmonary resuscitation facilitates cardiac and cerebral recovery after prolonged untreated ventricular fibrillation," Resuscitation, 2012, pp. 1-7.
Shapiro et al., "Neurosurgical Anesthesia and Intracranial Hypertension," Anesthesia, 3rd Edition, 1990, Church Livingston, New York, Chapter 54, pp. 1737-1789.
Yannopoulos et al., "Intrathoracic Pressure Regulator During Continuous-Chest-Compression Advanced Cardiac Resuscitation Improves Vital Organ Perfusion Pressures in a Porcine Model of Cardiac Arrest", Circulation, 2005, pp. 803-811.

(56) References Cited

OTHER PUBLICATIONS

Yannopoulos et al.,"Intrathoracic pressure regulation improves vital organ perfusion pressures in normovolemic and hypovolemic pigs," Resuscitation, 2006, pp. 445-453, vol. 70.

Yannopoulos et al., "Intrathoracic Pressure Regulation Improves 24- Hour Survival in a Porcine Model of Hypovolemic Shock," Anesthesia & Analgesia, ITPR and Survival in Hypovolemic Shock, 2007, pp. 157-162, vol. 104:1.

Yannopoulos et al., "Sodium nitroprusside enhanced cardiopulmonary resuscitation improves survival with good neurological function in a porcine model of prolonged cardiac arrest," Critical Care Medicine, 2011, pp. 1-6, vol. 39:6.

- Swine model: 12 female farm pigs (32±1Kg)
  – Anesthetic: ketamine followed by isoflurane
  – 6 min untreated VF
  – 3 min sequential CPR epochs
    • standard (S) CPR,
    • S-CPR + an impedance threshold device (ITD),
    • active compression decompression (ACD) + ITD CPR.

END-TIDAL CARBON DIOXIDE AND AMPLITUDE SPECTRAL AREA AS NON-INVASIVE MARKERS OF CORONARY PERFUSION PRESSURE

CROSS-REFERENCE TO RELATED APPLICATIONS

This application is a continuation of co-pending U.S. patent application Ser. No. 15/420,653, filed Jan. 31, 2017, which is a continuation of U.S. patent application Ser. No. 14/292,578, filed May 30, 2014, now abandoned, which claims priority to U.S. Provisional Patent Application No. 61/829,176 filed May 30, 2013, entitled END TIDAL CARBON DIOXIDE AND AMPLITUDE SPECTRAL AREA AS NON-INVASIVE MARKERS OF CORONARY PERFUSION PRESSURE AND ARTERIAL PRESSURE, the entire disclosures of which are hereby incorporated by reference, for all purposes, as if fully set forth herein.

SUMMARY

Amplitude Spectrum Area (AMSA) values during ventricular fibrillation (VF) correlate with myocardial energy stores and predict defibrillation success. AMSA calculations however require particular hardware and/or software, and are clinically not used to determine an optimal time to deliver a defibrillation shock. By contrast, end tidal $CO_2$ ($ETCO_2$) values provide a non-invasive assessment of circulation during cardiopulmonary resuscitation (CPR). Accordingly, it is contemplated that $ETCO_2$ measurements, alone or in combination with AMSA, values may be utilized as a non-invasive means to determine an optimal time to deliver defibrillation during cardiac arrest and CPR. This is supported by acquired data that demonstrates a positive correlation between AMSA and $ETCO_2$, as discussed throughout. In particular, it has been demonstrated that AMSA and $ETCO_2$ correlate with each other and can be used to correlate with myocardial perfusion. This correlation may be used as a way to provide additional support for more widespread use of $ETCO_2$ to help guide defibrillation therapy.

DETAILED DESCRIPTION

Figure 1:
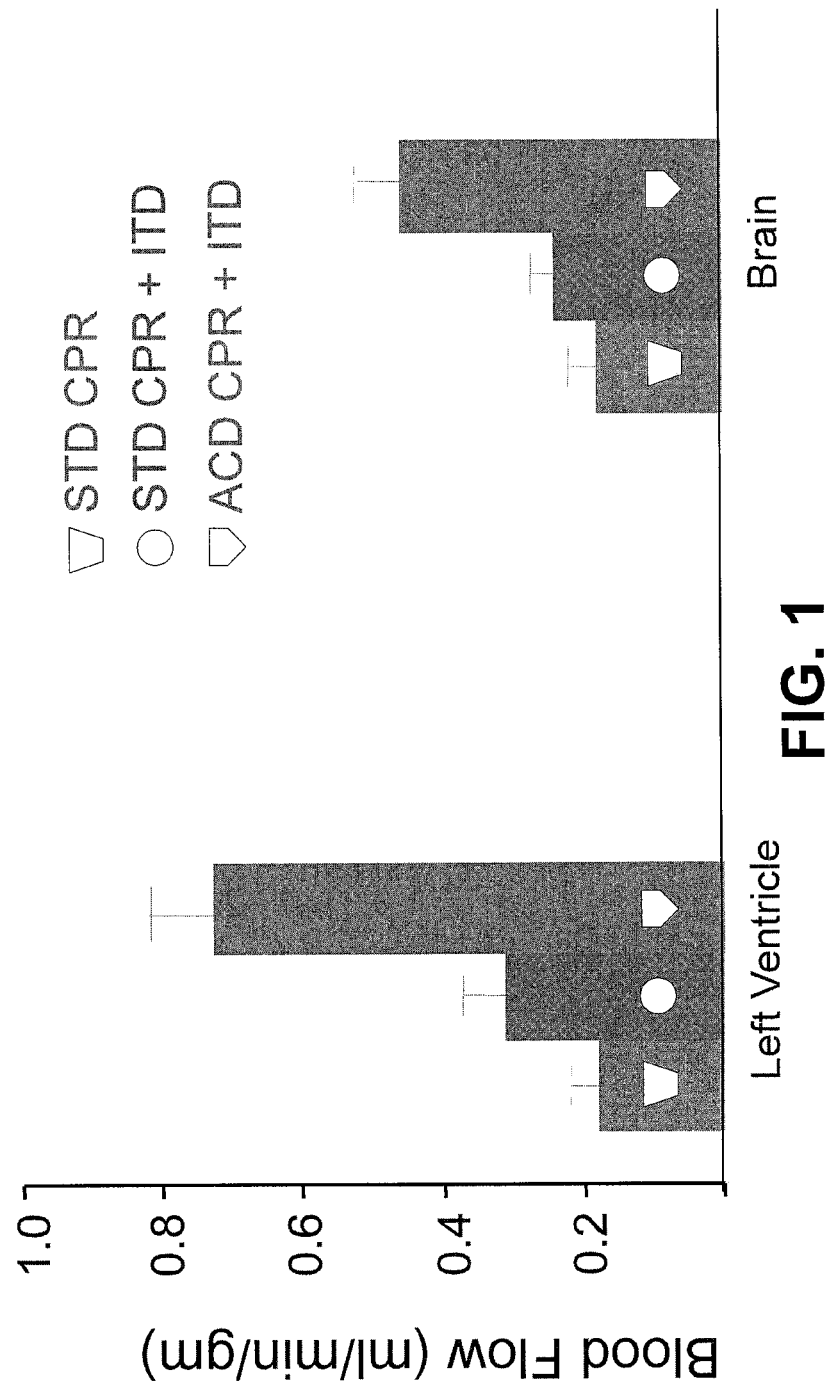
FIG. 1 shows blood flow during multiple different CPR methods (porcine VF model).

Using multiple CPR methods to generate several different levels of coronary perfusion and cerebral perfusion, a correlation between $ETCO_2$ and AMSA values is identified. The data establishes a firm correlation between $ETCO_2$ and AMSA, and demonstrates that $ETCO_2$ may be useful as an independent indicator as to when to deliver a defibrillation shock. In particular, in one example embodiment, $ETCO_2$ measurements may be used alone as a guide to determine when to defibrillate an individual. In another example embodiment, $ETCO_2$ measurements may be used in combination with AMSA values as a guide to determine when to defibrillate an individual. Although not so limited, an appreciation of the various aspects of the disclosure may be acquired from the following description in connection with the drawings.

The International Consensus on Cardiopulmonary Resuscitation 2010 recommends delivering a defibrillation shock every two minutes during treatment of cardiac arrest. The magnitude of the electrical energy of the delivered shock, however, has been demonstrated to be related to the severity of post-resuscitation global myocardial dysfunction. Additionally, interruptions in precordial compressions have been determined to reduce coronary perfusion pressures (CoPP) which may compromise the success of the shocks, especially after prolonged cardiac arrest. To limit the number of unnecessary shocks and interruptions in precordial compressions, VF waveform analysis has been established to predict the success of defibrillation at any given time. Several different analysis methods have been developed and the most efficient of these methodologies is to examine the AMSA values. The technique to determine AMSA values however is generally not instantaneous due to the need to sequentially sample and filter a large amount of electrocardiographic data and then perform multiple calculations. As such, AMSA is not recommended for routine use in the guideline for defibrillation management in adult cardiac arrest in the clinical setting in or out-of-hospital.

Establishing an accurate and rapid method to predict the success of defibrillation may have a substantial impact on the survival outcome of a patient. Several studies have demonstrated $ETCO_2$ values parallel changes in cardiac output, CoPP and myocardial perfusion while AMSA calculations are associated with CoPP. Since both AMSA and $ETCO_2$ are indicated to correlate with CoPP during cardiac arrest, one aspect of the disclosure is that $ETCO_2$ would reflect AMSA values during VF and CPR based upon the differences in flow as a consequence of the different methods of CPR. This association may provide a simple noninvasive means for medical practitioners to determine the optimal time for defibrillation. The present disclosure demonstrates a correlation between the parameters of $ETCO_2$ and AMSA. Specifically, three CPR methods, each generating a different level of perfusion, are utilized to establish the association between $ETCO_2$ and AMSA.

For example, FIG. 1 shows blood flow during CPR in the left ventricle and brain (porcine VF model) using a standard CPR procedure (STD CPR), a standard CPR procedure using an impedance threshold device (STD CPR+ITD), and an active compression-decompression CPR procedure using an impedance threshold device (ACD CPR+ITD). As shown in FIG. 1, magnitude of blood flow increases in order of: STD CPR (leftmost bar); STD CPR+ITD (middle bar); and ACD CPR+ITD (rightmost bar).

Figure 2:
FIG. 2 shows details of a model used to demonstrate AMSA and $ETCO_2$ correlation.

FIG. 2 shows detail of a swine model utilized to establish the association between $ETCO_2$ and AMSA. Twelve female farm pigs (32±1 kg) pigs (domestic crossbreed) were fasted overnight. They were sedated with 10 ml (100 mg/ml) of intramuscular ketamine HCl (Ketaset, Fort Dodge Animal Health, Fort Dodge, Iowa). An intravenous bolus of propofol (PropoFlo, Abbott Laboratories, North Chicago, Ill.) (2-3 mg/kg) was given via a lateral ear vein and then infused at a rate of 160-200 .mu.g/kg/min for the remainder of the preparatory phase. The animals were intubated with a 7.5 mm cuffed French endotracheal tube inflated to prevent air leaks. Positive pressure, volume control ventilation with a tidal volume of 10 ml/kg and room air was delivered with a NarkoMed 4A (North American Drager) ventilator. The respiratory rate was adjusted (average 12±2 bpm) to keep oxygen saturation above 96% and $ETCO_2$ between 38-42 mmHg. While in a ventral recumbent position, an intracranial bolt was inserted into the animal's parietal lobe to measure intracranial pressure using a 3.5 French micromanometer pressure transducer (Miko-Tip Transducer, Millar Instruments, Inc., Houston, Tex.). The animals were then placed supine. The left femoral artery and left external jugular vein were cannulated using a modified Seldinger percutaneous technique. Central aortic blood pressures were measured continuously via a micromanometer-tipped Millar catheter placed in the chest cavity at the level of origin of the thoracic descending aorta. Central venous blood pressures were measured via a micromanometer-tipped Millar catheter placed in the superior vena cava, approximately 2 cm above the right atrium. Right atrial pressures were maintained between 5-7 mmHg during the preparatory phase. Carotid artery blood flows were measured using a bidirectional Doppler flow probe attached to the internal carotid artery (Transonic Systems, Ithaca, N.Y.). Surface ECG was also monitored continuously. A thermometer was placed in the rectum and body temperature maintained with a heating blanket between 37.0.degree. C. and 38.0.degree. C. during pre-study and post-ROSC phases. All data were or was digitized using a computer data analysis program (BIOPAC MP 150, BIOPAC Systems Inc., Calif.). $ETCO_2$, tidal volume, and arterial oxygen saturation were recorded with a $CO_2SMO$ Plus (Novametrix Medical Systems, Wallingford, Conn.).

Following preparation, the animals were positioned for CPR and pre-arrest hemodynamic variables were measured. Ventricular fibrillation was induced in the anesthetized animal with application of a 50 Hz, 7.5 V AC electrical current through an electrophysiology catheter to the endocardial surface of the right ventricle. Propofol anesthesia was decreased to a rate of 100 .mu.g/kg/min and remained at this level during CPR. After 6 minutes of untreated cardiac arrest, mechanical CPR via a pneumatic piston attached to a compression pad was initiated. Chest compressions were performed with a rate of 100/min and a depth of 25% of the anteroposterior diameter as previously described. All animals were ventilated during CPR with supplemental oxygen (2 LPM) with a bag-valve resuscitator at a compression to ventilation ratio of 10:1 and a tidal volume of 10 ml/kg. As shown in FIG. 2, CPR was performed for a total of 9 minutes; 3 minutes of STD CPR, 3 minutes of STD CPR+ impedance threshold device (ITD) (ResQPOD, Advanced Circulatory Systems Inc., Roseville, Minn., USA), and 3 minutes of active compression decompression (ACD) CPR+ ITD. The transition from one method of CPR to the next was made in an uninterrupted manner. ACD CPR was performed using a suction cup attached to the pneumatic piston as previously described. After the 9 minutes of CPR, epinephrine (40 .mu.g/Kg) was administered intravenously and 1 minute later the pigs were defibrillated with up to 3 additional sequential 200 Joule transthoracic biphasic shocks. Following successful resuscitation and one hour of observation, the animal was given a bolus of propofol (100 mg) and euthanized with a bolus intravenous injection of 10M KCl (30 mg/Kg).

As part of data analysis, the electrocardiographic (ECG) signal was sampled at 300 Hz and stored in 1.6 second increments such that each 4 second wavelet was processed at intervals of 1.6 seconds. The ECG signal was filtered between 3 and 30 Hz to minimize low frequency artifacts produced by precordial compression and to exclude the electrical interference of ambient noise at frequencies greater than 48 Hz. Analog ECG signals were digitized and converted from a time domain to a frequency domain by fast Fourier transformation via a computer data analysis program (BIOPAC). Utilizing MATLAB 5.1 software (Mathworks Inc., Natick, Mass.), the sum of individual amplitudes and frequencies resulted in the amplitude spectrum area (i.e., AMSA). Power spectrums for the VF waveform were generated the same way.

The mean AMSA for each pig for each intervention was used for the analysis. The mean values for all hemodynamic parameters extracted from multiple 4 second intervals obtained contemporaneously with the AMSA data were measured and used for future analysis. All values with a non-normal distribution are expressed as Median (25:75 percentiles). A Friedman statistical test was conducted to analyze $ETCO_2$, AMSA, the calculated coronary and cerebral perfusion pressure, aortic systolic, diastolic and mean pressure, right atrial pressure and intracranial pressure during the three CPR methods. Coronary perfusion pressures were determined by the difference between the diastolic aortic pressure and diastolic right atrial pressure during each CPR intervention. Cerebral perfusion pressures were determined by taking the difference between the aortic pressure and the intracranial pressure. Spearman correlation and Friedman tests were used to analyze the correlation between the different hemodynamic parameters. A Bland and Altman assessment was used to compare $ETCO_2$ and AMSA values with a range of agreement defined as mean bias±1.96 SD. P values of <0.05 were considered statistically significant. Statistical analyses were performed with SPSS® Statistics 17.0 (IBM Corporation, Somers, N.Y., USA).

In review of results, it was found that there were significant differences in the $ETCO_2$, AMSA, coronary perfusion pressure, cerebral perfusion pressure, systolic aortic pressure, mean aortic pressure, mean right atrial pressure and mean intracranial pressure based upon the method of CPR used. The key perfusion parameters were lowest with STD CPR, increased with STD CPR+ITD, and were highest with ACD CPR+ITD, as shown in Table 1:

TABLE 1

| | $ETCO_2$ | AMSA | Ao sys | Ao dia | Ao mean | RA mean | ICP mean | CePP | CoPP | CBF |
|---|---|---|---|---|---|---|---|---|---|---|
| STD CPR | 5.7 (4.5; 7.9)* | 31.1 (26.9; 39.4)* | 30.7 (28.3; 35.2)* | 9.5 (8.4; 12.1) | 20.2 (18.2; 22.4)* | 12.6 (11.4; 15.7)* | 18.3 (14.8; 22)* | 2.8 (1.4; 8.1)* | 8.4 (6.1; 10)* | 25 (14; 36) |
| STD CPR + | 15.2 (13.9; | 39.7 (29.9; | 37.7 (33; | 10.5 (8.9; | 22.9 (22; | 15.5 (13.4; | 19.6 (16.2; | 5.7 (3.2; | 10.6 (7.9; | 24 (14; |

TABLE 1-continued

|  | ETCO$_2$ | AMSA | Ao sys | Ao dia | Ao mean | RA mean | ICP mean | CePP | CoPP | CBF |
|---|---|---|---|---|---|---|---|---|---|---|
| ITD | 18.4) | 45.8) | 64.7) | 19.4) | 39.9) | 27.5) | 23.7) | 14.8) | 13.3) | 29) |
| ACD CPR + LID | 20.5 (16.5; 21.5) | 45.5 (31.5; 50.8) | 41.9 (37; 59.9) | 11.5 (7.6; 18) | 25.9 (23.7; 34.1) | 16.6 (14.1; 22.3) | 18.4 (15.2; 22.9) | 7.6 (4.9; 17) | 13.3 (7.9; 19.7) | 27 (19; 45) |

Median (25; 75 percentile); hemodynamic parameter using the three different cardiopulmonary resuscitation techniques.
Ao sys: systolic aortic pressure;
Ao dia: diastolic aortic pressure;
Ao mean: mean aortic pressure;
RA mean: mean right atrial pressure;
ICP mean: mean intracranial pressure;
CePP: cerebral perfusion pressure;
CoPP: Coronary perfusion pressure;
ETCO$_2$: end tidal CO$_2$ (mmHg);
AMSA: amplitude spectral area (mV-Hz);
CBF: Mean carotid blood flow (ml/min);
*p = 0.001 STD CPR < STD CPR + ITD < ACD CPR + ITD (Friedman statistical test).

Figure 3:
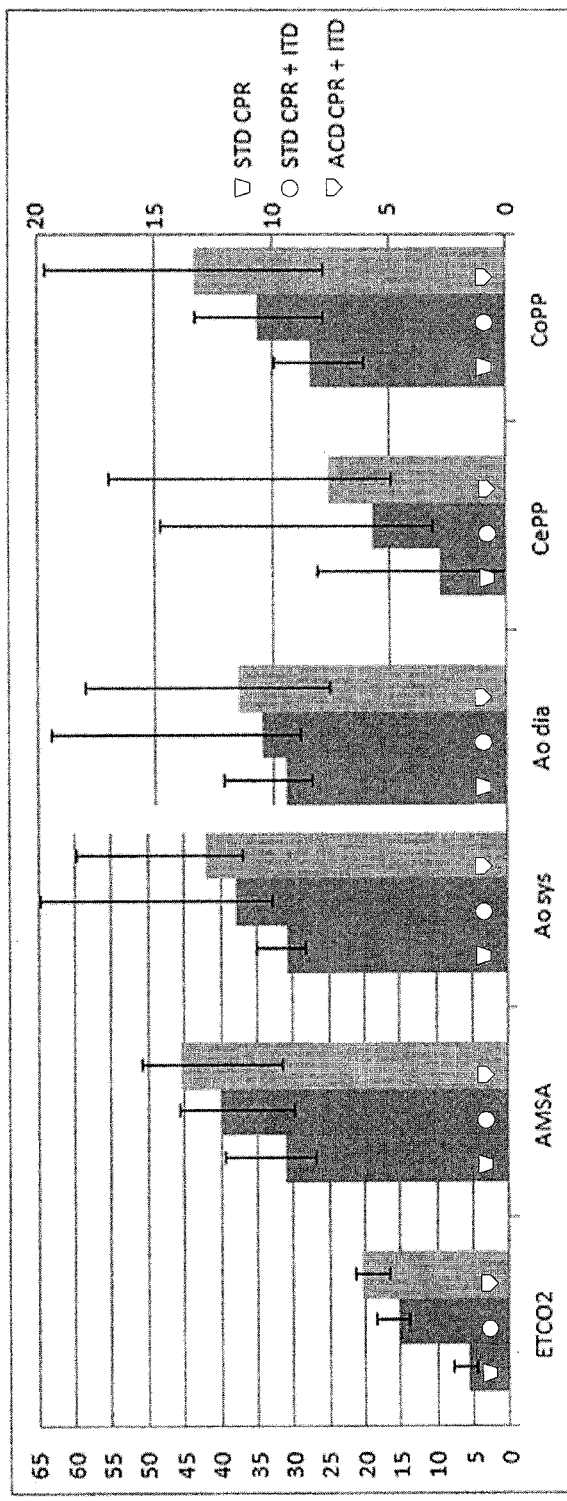
FIG. 3 shows parameter results using three different CPR techniques.

The data of Table 1 is shown graphically in FIG. 3. STD CPR (leftmost bar); STD CPR+ITD (middle bar); and ACD CPR+ITD (rightmost bar).

Figure 4:
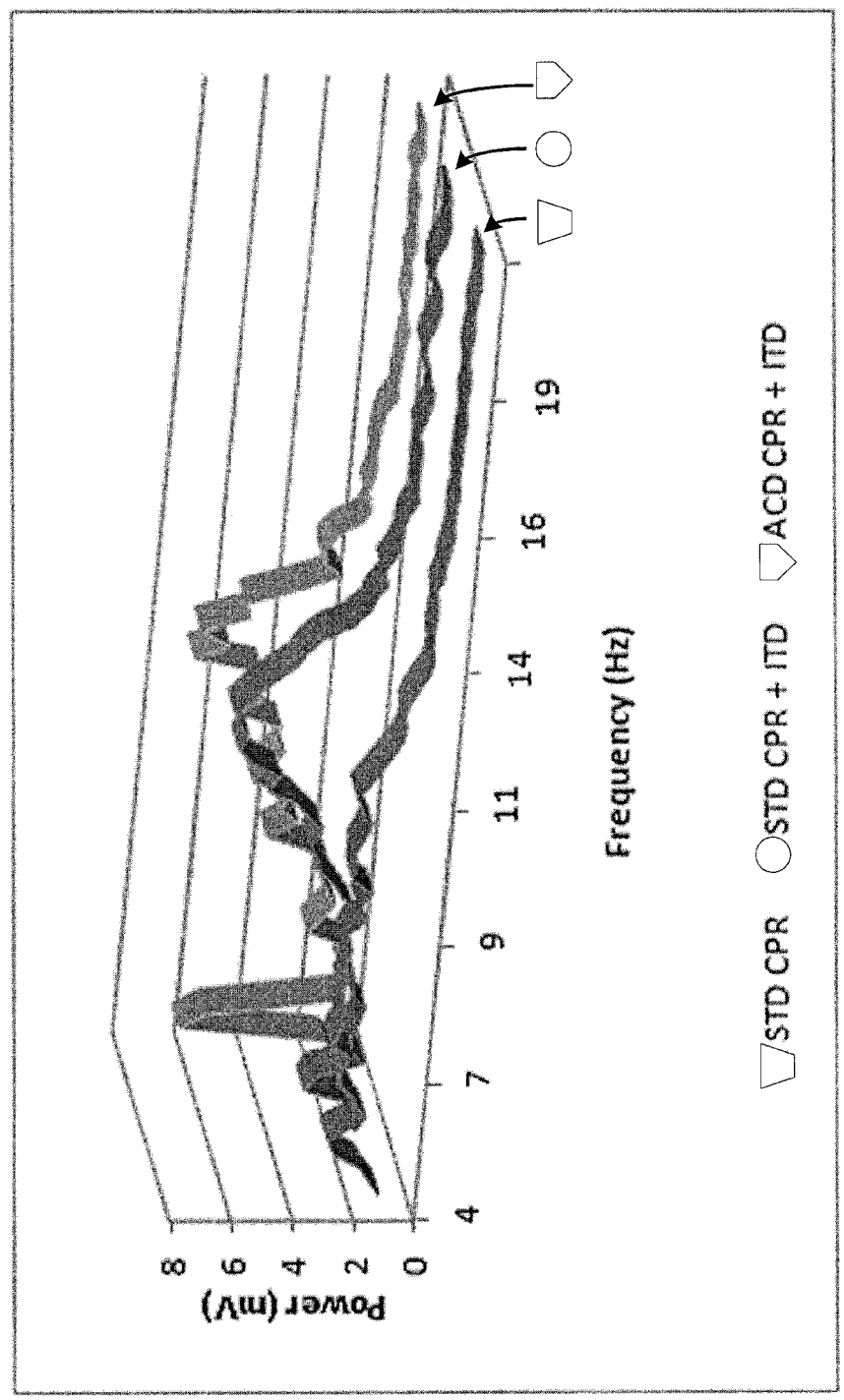
FIG. 4 shows a representative spectrum from a porcine model during each of three methods of CPR.

The power spectrum for the VF waveform also changed significantly based upon the method of CPR. FIG. 4 shows a representative spectrum from one pig during each of the 3 methods of CPR, STD CPR (frontmost curve or trend); STD CPR+ITD (middle curve or trend); and ACD CPR+ITD (rearmost curve or trend). There was a pronounced increase in the high frequency signal in this representative study and when the respective values for all animals were averaged.

Figure 5:
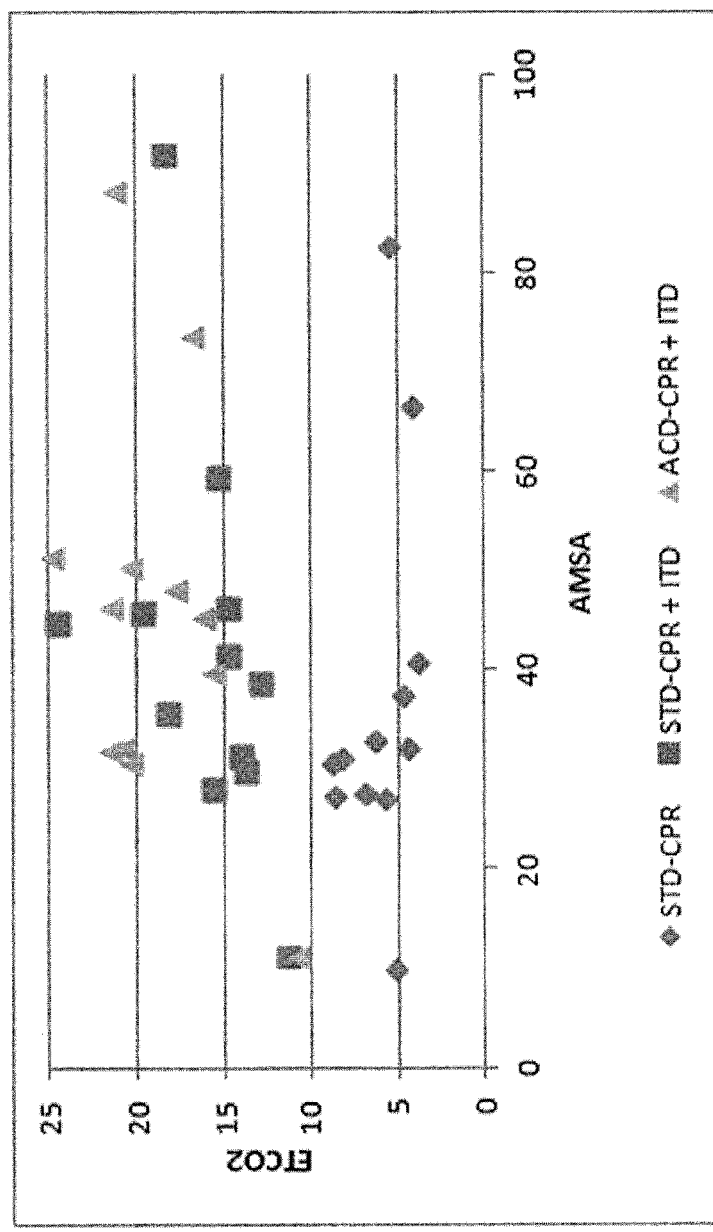
FIG. 5 demonstrates a correlation between AMSA and $ETCO_2$.

Further analysis demonstrated a correlation between AMSA and ETCO$_2$ (r=0.374, p=0.025) and a correlation between AMSA and key hemodynamic parameters (coronary perfusion pressure, cerebral perfusion pressure, aortic systolic, diastolic and mean pressure) (p<0.05), as shown in Table 2:

FIG. 5 demonstrates the correlation between AMSA and ETCO$_2$: STD CPR (diamond); STD CPR+ITD (square); and ACD CPR+ITD (triangle).

Figure 6:
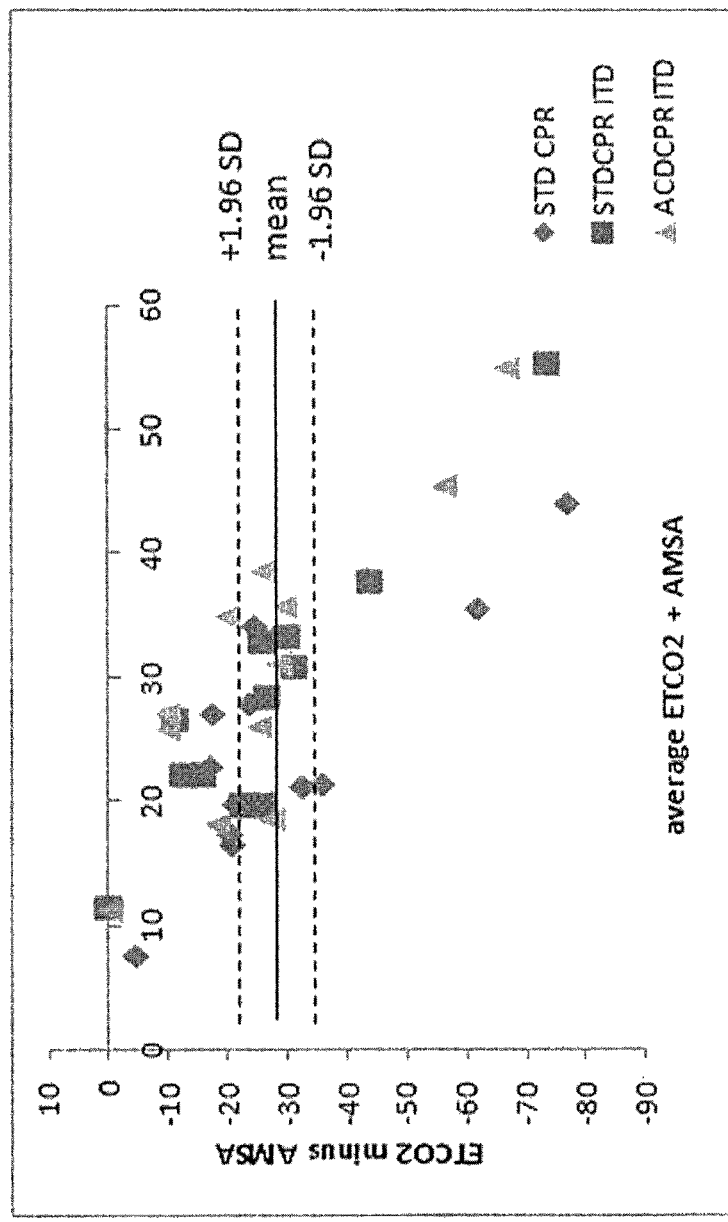
FIG. 6 shows results of Bland-Altman analysis indicating the 95% limits of agreement between AMSA and $ETCO_2$ ranged from −21.4 to −33.5.

The Bland-Altman analysis indicated the 95% limits of agreement between AMSA and ETCO ranged from −21.4 to −33.5. This is shown graphically in FIG. 6: STD CPR (diamond); STD CPR+ITD (square); and ACD CPR+ITD (triangle). These study results indicate a strong association between AMSA and ETCO$_2$.

Research has conventionally focused on finding a non-invasive method to predict the success of defibrillation with the hope of having a substantial impact on the survival outcome of patients. AMSA has been reported to provide an 86% positive and an 85% negative predictive value, respectively for a threshold value at 21 mV x Hz. However AMSA values can be difficult to calculate in real-time and are not recommended for routine use in the guideline for defibrillation management in adult cardiac arrest in the clinical

TABLE 2

|  | AMSA | Ao sys | Ao dia | Ao mean | CePP | CoPP | CBF |
|---|---|---|---|---|---|---|---|
| ETCO$_2$ | 0.374* 0.025 | 0.709* <0.001 | 0.315 0.061 | 0.723* <0.001 | 0.526* 0.001 | 0.340* 0.043 | 0.295 0.08 |
| AMSA |  | 0.541* 0.001 | 0.487* 0.003 | 0.612* <0.001 | 0.217 0.203 | 0.185 0.281 | 0.639* <0.001 |
| Ao sys |  |  | 0.611* <0.001 | 0.953* <0.001 | 0.825* <0.001 | 0.514* 0.001 | 0.567* <0.001 |
| Ao dia |  |  |  | 0.709* <0.001 | 0.499* 0.002 | 0.514* 0.001 | 0.411* 0.006 |
| Ao Mean |  |  |  |  | 0.77* <0.001 | 0.575* <0.001 | 0.597* <0.001 |
| CePP |  |  |  |  |  | 0.503* 0.002 | 0.373* <0.001 |

Ao Ao Ao AMSA sys dia mean CePP CoPP CBF ETCO2 0.374* 0.709* 0.315 0.723* 0.526* 0.340* 0.295 0.025 <0.001 0.061 <0.001 0.001 0.08 AMSA 0.541* 0.487* 0.612* 0.217 0.185 0.639* 0.001 0.003 <0.001 0.203 0.281 <0.001 Ao 00.611* 0.953* 0.825* 0.514* 0.567* sys <0.001 <0.001 <0.001 0.001 <0.001 Ao 0.709* 0.499* 0.514* 0.411* dia <0.001 0.002 0.001 0.006 Ao 0.77* 0.575* 0.597* mean <0.001 <0.001 <0.001 CePP 0.503* 0.373* 0.002 <0.001
Correlation between the different hemodynamic parameter, rs and p, *correlation is significant.
Ao sys: systolic aortic pressure;
Ao dia: diastolic aortic pressure;
Ao mean: mean aortic pressure;
RA mean: mean right atrial pressure;
ICP mean: mean intracranial pressure;
CePP: cerebral perfusion pressure;
CoPP: Coronary perfusion pressure;
ETCO$_2$: end tidal CO2 (mmHg);
AMSA: amplitude spectral area (mV-Hz);
CBF: Mean carotid blood flow (ml/min). Those are r.

setting in or out-of-hospital. By contrast, continuous $ETCO_2$ waveforms are readily obtainable and can be rapidly analyzed. Using three different methods of CPR to consistently vary different organ perfusion levels, a correlation between $ETCO_2$ and AMSA is demonstrated. Because of this newly discovered correlation, techniques for using $ETCO_2$ values, alone or in combination with AMSA values, to direct a caregivers are proposed as to when to apply a defibrillating shock. More specifically, if the measured $ETCO_2$ values are within an acceptable range or near an acceptable value, an indication may be supplied to the caregiver as to when to apply a defibrillating shock.

Figure 7:
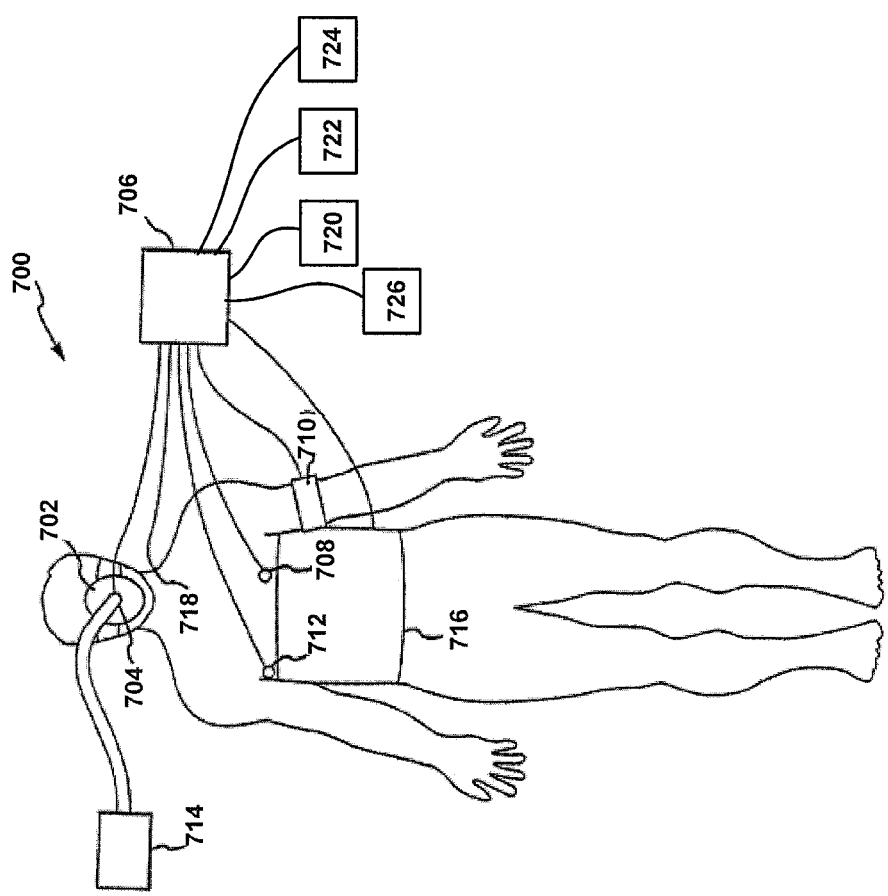
FIG. 7 shows an example treatment system in accordance with the present disclosure.

FIG. 7 shows an example treatment system 700 in accordance with the present disclosure. The system 700 may include a facial mask 702 and a valve system 704. The valve system 704 may be coupled to a controller 706. In turn, the controller 706 may be used to control an impedance level of the valve system 704. The level of impedance may be varied based on measurements of physiological parameters, or using a programmed schedule of changes. The system 700 may include a wide variety of sensors and/or measuring devices to measure any of a number physiological parameters. Such sensors or measuring devices may be integrated within or coupled to the valve system 704, the facial mask 702, etc., or may be separate depending on implementation. An example of sensors and/or measuring devices may include a pressure transducer for taking pressure measurements (such as intrathoracic pressures, intracranial pressures, intraocular pressures), a flow rate measuring device for measuring the flow rate of air into or out of the lungs, or a $CO_2$ sensor for measuring expired $CO_2$. Examples of other sensors or measuring devices include a heart rate sensor 708, a blood pressure sensor 710, and a temperature sensor 712. These sensors may also be coupled to the controller 706 so that measurements may be recorded. Further, it will be appreciated that other types of sensors and/or devices may be coupled to the controller 706 and may be used to implement defibrillation and measure various physiological parameters, such as bispectral index, oxygen saturation and/or blood levels of $O_2$, blood lactate, blood pH, tissue lactate, tissue pH, blood pressure, pressures within the heart, intrathoracic pressures, positive end expiratory pressure, respiratory rate, intracranial pressures, intraocular pressures, respiratory flow, oxygen delivery, temperature, end-tidal $CO_2$, tissue $CO_2$, cardiac output, and many others.

For example, ECG electrode(s) or sensor(s) 720 may also be coupled to the controller 706 so that measurements related to the electrical activity of an individual's heart may be monitored and recorded. Advantageously, this may allow for the acquisition and/or derivation of AMSA values of a particular individual during a CPR procedure, as discussed throughout the present disclosure. Additionally, a display screen 722 and one or more speakers 724 may be coupled to the controller 706 to provide a prompt to a rescuer, such as a prompt to "cue" a rescuer to defibrillate an individual while CPR is performed on the individual. Such a feature is discussed in further detail in connection with at least FIG. 8. Even further, one or more electrodes 726 may be coupled to the controller 706 to enable application of a defibrillation shock(s) either automatically (e.g., without direct user-input) or manually (e.g., in response to activation of a particular "button"). Still many other devices, sensors, etc., may be coupled to the controller 706 as needed or desired, to implement the various features or aspects of the present disclosure.

In some cases, the controller 706 may be used to control the valve system 704, to control any sensors or measuring devices, to record measurements, and to perform any comparisons. Alternatively, a set of computers and/or controllers may be used in combination to perform such tasks. This equipment may have appropriate processors, display screens, input and output devices, entry devices, memory or databases, software, and the like needed to operate the system 700. A variety of devices may also be coupled to controller to cause the person to artificially inspire. For example, such devices may comprise a ventilator 714, an iron lung cuirass device 716 or a phrenic nerve stimulator 718. The ventilator 714 may be configured to create a negative intrathoracic pressure within the person, or may be a high frequency ventilator capable of generating oscillations at about 200 to about 2000 per minute. Other embodiments are possible.

Figure 8:
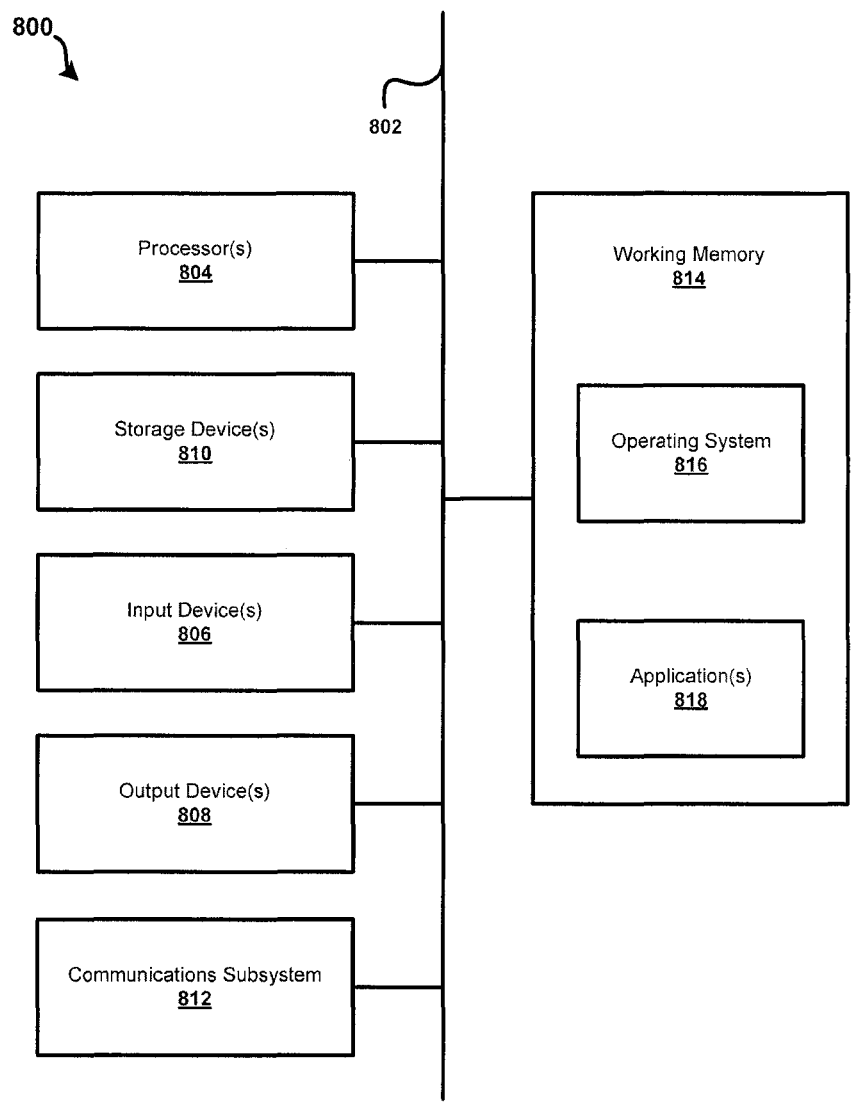
FIG. 8 shows an example computing system or device.

FIG. 8 shows an example computer system or device 800 in accordance with the present disclosure. An example of a computer system or device includes a medical device, a desktop computer, a laptop computer, a tablet computer, and/or any other type of machine configured for performing calculations. The example computer device 800 may be configured to perform and/or include instructions that, when executed, cause the computer system 800 to perform a method for providing a guide to determine when to defibrillate an individual using $ETCO_2$ measurements alone. The example computer device 800 may be configured to perform and/or include instructions that, when executed, cause the computer system 800 to perform a method for providing a guide to determine when to defibrillate an individual using $ETCO_2$ measurements and AMSA values. The particular trigger of when to provide the shock may be based on part on the correlation between the $ETCO_2$ measurements and predetermined AMSA values, or may be determined empirically based on test data using $ETCO_2$ measurements. It is thus contemplated that the example computer device 800 may be coupled to one or more sensors configured and arranged to acquire and/or operate on such measurements or data, itself have integrated therein one or more sensors configured and arranged to acquire and/or operate on such measurements or data, or any combination thereof.

Furthermore, it is contemplated that the example computer system 800 may include or comprise at least one of an audio speaker and a display monitor so as to provide at least one of an audio indication (e.g., a particular tone or series of tones such as a single or periodic or intermittent "beep," a particular word such as a "go" or "defibrillate," and etc.) and a visual indication (e.g., a particular colored screen or series of screens such as a "green" screen or periodically or intermittently "flashing" screens of one or more particular colors, a particular graphic such as a "go" or "defibrillate," and etc.) so that a medical professional or other individual may be "cued" to defibrillate an individual during CPR as performed on the individual as discussed throughout the present disclosure. Such features may be embodied by the output device(s) 808 shown in FIG. 8 discussed further below.

The computer device 800 is shown comprising hardware elements that may be electrically coupled via a bus 802 (or may otherwise be in communication, as appropriate). The hardware elements may include a processing unit with one or more processors 804, including without limitation one or more general-purpose processors and/or one or more special-purpose processors (such as digital signal processing chips, graphics acceleration processors, and/or the like); one or more input devices 806, which may include without limitation a remote control, a mouse, a keyboard, and/or the like; and one or more output devices 808, which may include without limitation, a video monitor or screen, an audio speaker, a printer, and/or the like.

The computer system 800 may further include (and/or be in communication with) one or more non-transitory storage devices 810, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer device 800 might also include a communications subsystem 812, which may include without limitation a modem, a network card (wireless or wired), an infrared communication device, a wireless communication device, and/or a chipset, such as a Bluetooth™ device, an 802.11 device, a WiFi device, a WiMax device, hardwired and/or wireless communication facilities, and/or the like. The communications subsystem 812 may permit data to be exchanged with a private and/or non-private network, other computer systems, and/or any other devices described herein. In many embodiments, the computer system 800 may further comprise a working memory 814, which may include a random access memory and/or a read-only memory device, as described above.

The computer device 800 also may comprise software elements, shown as being currently located within the working memory 814, including an operating system 816, device drivers, executable libraries, and/or other code, such as one or more application programs 818, which may comprise computer programs provided by various embodiments, and/or may be designed to implement methods, and/or configure systems, provided by other embodiments, as described herein. By way of example, one or more procedures described with respect to the method(s) discussed above, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code might be stored on a non-transitory computer-readable storage medium, such as the storage device(s) 810 described above. In some cases, the storage medium might be incorporated within a computer system, such as computer system 800. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer device 800 and/or might take the form of source and/or installable code, which, upon compilation and/or installation on the computer system 800 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer device 800) to perform methods in accordance with various embodiments of the invention. According to a set of embodiments, some or all of the procedures of such methods are performed by the computer system 800 in response to processor 804 executing one or more sequences of one or more instructions (which might be incorporated into the operating system 816 and/or other code, such as an application program 818) contained in the working memory 814. Such instructions may be read into the working memory 814 from another computer-readable medium, such as one or more of the storage device(s) 810. Merely by way of example, execution of the sequences of instructions contained in the working memory 814 may cause the processor(s) 804 to perform one or more procedures of the methods described herein.

The terms "machine-readable medium" and "computer-readable medium," as used herein, may refer to any medium that participates in providing data that causes a machine to operate in a specific fashion. In an embodiment implemented using the computer device 800, various computer-readable media might be involved in providing instructions/code to processor(s) 804 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 810. Volatile media may include, without limitation, dynamic memory, such as the working memory 814.

Example forms of physical and/or tangible computer-readable media may include a floppy disk, a flexible disk, hard disk, magnetic tape, or any other magnetic medium, a CD-ROM, any other optical medium, a RAM, a PROM, EPROM, a FLASH-EPROM, any other memory chip or cartridge, or any other medium from which a computer may read instructions and/or code.

Various forms of computer-readable media may be involved in carrying one or more sequences of one or more instructions to the processor(s) 804 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 800.

The communications subsystem 812 (and/or components thereof) generally will receive signals, and the bus 802 then might carry the signals (and/or the data, instructions, etc. carried by the signals) to the working memory 814, from which the processor(s) 804 retrieves and executes the instructions. The instructions received by the working memory 814 may optionally be stored on a non-transitory storage device 810 either before or after execution by the processor(s) 804.

As may be understood from the foregoing discussion in connection with the drawings, it is contemplated that $ETCO_2$ measurements may be used alone as a guide to determine when to defibrillate an individual. Alternatively, $ETCO_2$ measurements may be used in combination with amplitude spectral area measurements as a guide to determine when to defibrillate an individual.

In particular, in some aspects, a computer-implemented method may include or comprise obtaining, by a computing or measuring system, an $ETCO_2$ measurement of an individual during a CPR procedure performed on the individual. The method may further include or comprise comparing, by the computing system, a particular $ETCO_2$ value derived from the $ETCO_2$ measurement to a predetermined threshold value. The method may further include or comprise providing, by the computing system based on the comparing, a perceivable indication that designates a time to deliver a defibrillation shock to the individual. Further, the computing system may, in some embodiments, use a change from one time point to the next or another, in $ETCO_2$ measurements, to determine the time to delivery of a defibrillation shock. The $ETCO_2$ measurements could include peak and/or trough $ETCO_2$ values, mean values, or $ETCO_2$ waveform characteristics which are affected by the amount of blood circulating or in circulation during CPR in the individual.

Additionally, or alternatively, the method may include or comprise providing the indication when the particular $ETCO_2$ value is less than or equal to the predetermined threshold value. For example, when $ETCO_2$ levels are persistently less than 10 mmHg, then the chances for a successful defibrillation may be considered to be extremely low and such information may be used by the computing system to determine that a defibrillatory shock should not be delivered at that time. Additionally, or alternatively, the method may include or comprise providing the indication when the particular $ETCO_2$ value is greater than or equal to the predetermined threshold value.

Additionally, or alternatively, the method may include or comprise providing, by the computing system based on the comparison, at least one of an audio indication and a visual indication that designates the time to deliver the defibrillation shock to the individual. The visual indication could be provided in the form of an absolute number or a graph of changes in $ETCO_2$ or a derivative of $ETCO_2$ over time, with an indication for the threshold value needed before a shock should be delivered.

Additionally, or alternatively, the method may include or comprise obtaining an electrocardiogram (ECG) measurement of the individual during the CPR procedure; deriving from the ECG measurement an amplitude spectral area value; and providing the indication that designates the time to deliver the defibrillation shock to the individual based upon the amplitude spectrum area value and the comparison of the $ETCO_2$ value to the predetermined threshold value. For example, both AMSA and $ETCO_2$ values would have to be at a threshold value before a shock is delivered, thereby providing the greatest likelihood for a successful defibrillation and survival. In this manner, the computing system may take into account both measurements before advising or triggering a defibrillatory shock. Other potential combinations of these two distinctly different physiological signals to provide a greater degree of predictive certainty of defibrillation success or failure include the value obtained by multiplying, or performing another mathematical operation, the $ETCO_2$ and AMSA values together to achieve a number that would provide an indicator that defibrillation would be successful.

In some aspects, a method may include or comprise performing a cardiopulmonary resuscitation (CPR) procedure on an individual; and delivering a defibrillation shock to the individual at a particular time based upon an indication provided by a computing system when a particular end-tidal carbon dioxide ($ETCO_2$) value derived from an $ETCO_2$ measurement of the individual during the CPR procedure is determined by the computing system as less than or greater than a predetermined threshold value. In some embodiments, once the rescuer observes the indication, then they would deliver the defibrillatory shock within the next 30-60 seconds. In cases where the shock is not successful, a follow-up $ETCO_2$ value could be used to determine if an additional 1-2 minutes of CPR is needed or whether the rescuer should charge the defibrillator and immediately deliver another shock. Thus, the post shock $ETCO_2$ value could be used to help determine the timing of follow up shocks if the first one is not successful. The computing system may adjust for the failed shock such that the next shock would not be advised unless the $ETCO_2$ values were higher, for example, 10% higher than those measured prior to the first shock.

Additionally, or alternatively, the method may include or comprise performing an intrathoracic pressure regulation procedure or a reperfusion injury protection procedure at or during the CPR procedure. Additionally, or alternatively, the method may include or comprise periodically extracting respiratory gases from the airway of the individual to create an intrathoracic vacuum that lowers pressure in the thorax to at least one of: enhance the flow of blood to the heart of the individual; lower intracranial pressures of the individual; and enhance cerebral profusion pressures of the individual. Additionally, or alternatively, the method may include or comprise preventing air from at least temporarily entering the lungs of the individual during at least a portion of a relaxation or decompression phase of the CPR procedure to create an intrathoracic vacuum that lowers pressure in the thorax to at least one of: enhance flow of blood to the heart of the particular individual; lower intracranial pressures of the particular individual; and enhance cerebral profusion pressures of the individual. The methods and devices used to perform CPR could include manual closed chest CPR, CPR with an active compression decompression device, and such CPR methods could be used together with an impedance threshold device to transiently impede inspiratory flow during the recoil phase of CPR or an intrathoracic pressure regulatory to actively extract gases form the lungs.

Additionally, or alternatively, the method may include or comprise performing a standard CPR procedure on the individual. Additionally, or alternatively, the method may include or comprise performing a stutter CPR procedure on the individual to achieve some degree of reperfusion injury protection. Additionally, or alternatively, the method may include or comprise performing an active compression-decompression CPR procedure on the individual. Additionally, or alternatively, the method may include or comprise positioning a mechanical CPR device relative to the chest of the individual; and activating the mechanical CPR device to perform a mechanized CPR procedure on the individual. Such CPR devices could include, but would not be limited to, a LUCAS device (Physio-control, Redmond, Wash.). The Zoll Autopulse (Chelmsford, Mass.), the Michigan Instrument Thumper (Grand Rapids, Mich.).

Additionally, or alternatively, the method may include or comprise delivering the defibrillation shock to the individual upon perception of the indication provided by the computing system at the particular time based upon an amplitude spectrum area value of the individual as derived from a measurement during the CPR procedure and when the particular $ETCO_2$ value is determined as less than or equal, or greater than or equal to the predetermined threshold value. Additionally, or alternatively, the method may include or comprise delivering the defibrillation shock to the individual upon perception of at least one of an audio indication and a visual indication provided by the computing system.

In some aspects, a system, device, or apparatus may include or comprise a first device that monitors concentration of carbon dioxide in respiratory gases of an individual at least during a cardiopulmonary resuscitation (CPR) procedure performed on the individual; a second device that compares a particular end-tidal carbon dioxide value derived from the concentration of carbon dioxide in respiratory gases of the individual to a predetermined threshold value; and a third device that provides based on the comparison a perceivable indication that designates a time to deliver a defibrillation shock to the individual. The second device may be used with the third device to determine the optimal time to deliver the shock and, if the first shock fails, may use the same or different logic to determine the time to deliver additional shocks.

Additionally, or alternatively, the system, device, or apparatus may include or comprise an electroencephalogram (EEG) sensor that measures an EEG signal of the individual at least during the CPR procedure performed on the individual, wherein the second device derives an amplitude spectrum area value from the EEG signal, and the third device provides the perceivable indication based upon the amplitude spectrum area value and the comparison of the particular end-tidal carbon dioxide value to the predetermined threshold value. Additionally, or alternatively, the system, device, or apparatus may include or comprise a circulation enhancement device that enhances circulation of the individual at least during the CPR procedure performed on the individual.

The methods, systems, and devices discussed above are examples. Various configurations may omit, substitute, or add various method steps or procedures, or system components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the example embodiments described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A defibrillation device for guiding defibrillation therapy of an individual during resuscitation, comprising:
    an end-tidal carbon dioxide ($ETCO_2$) sensor for obtaining signals representing $ETCO_2$ of the individual;
    an electrocardiogram (ECG) sensor for obtaining signals representing ECG of the individual; and
    a processor in communication with the $ETCO_2$ sensor and the ECG sensor and configured to:
        receive and process the signals representing $ETCO_2$ from the $ETCO_2$ sensor to generate $ETCO_2$ data,
        receive and process the signals representing ECG from the ECG sensor to generate ECG data,
        analyze the $ETCO_2$ data and the ECG data, the analysis of the ECG data being frequency-based,
        determine, based on the analysis of the $ETCO_2$ data and the ECG data, whether a defibrillation shock should be delivered to the individual, and
        provide an indication that designates whether the defibrillation shock should be delivered.

2. The device of claim 1, wherein the determination is based on whether the $ETCO_2$ data is higher or lower than a first predetermined threshold value.

3. The device of claim 2, wherein the predetermined threshold value is from 5 mmHg to 20 mmHg.

4. The device of claim 1, wherein the processor is configured to perform a frequency domain transform on the ECG data.

5. The device of claim 4, wherein the frequency domain transform results in an amplitude spectrum area (AMSA) value.

6. The device of claim 5, wherein the determination is further based on whether the AMSA value is higher or lower than a second predetermined threshold value.

7. The device of claim 6, wherein the second predetermined threshold value is from 31 mV-Hz to 45 mV-Hz.

8. The device of claim 1, wherein the determination is based on analysis of both the ECG data and the $ETCO_2$ data.

9. The device of claim 8, wherein the determination is based on a comparison of the ECG data to a first predetermined threshold and a comparison of the $ETCO_2$ data to a second predetermined threshold value.

10. The device of claim 1, further comprising a display, and wherein the processor is configured to provide the indication of whether the defibrillation shock should be delivered on the display.

11. The device of claim 10, wherein the indication comprises a prompt on the display instructing a user as to the proper time to deliver the defibrillating shock.

12. The device of claim 1, further comprising one or more speakers for providing the indication of whether the defibrillation shock should be delivered.

13. The device of claim 12, wherein the indication comprises a prompt instructing a user as to a proper time to deliver the defibrillating shock.

14. The device of claim 1, further comprising a defibrillator.

15. The device of claim 14, further comprising further comprising defibrillation electrodes.

16. The device of claim 14, wherein the processor is configured to instruct the defibrillator to provide the defibrillating shock based on the determination.

17. The device of claim 1, further comprising one or more additional sensors.

18. The device of claim 17, wherein the one or more additional sensors are one or more of a heart rate sensor, a blood pressure sensor, a temperature sensor, a bispectral index sensor, an oxygen sensor, a blood lactate sensor, a blood pH sensor, a tissue lactate sensor, a tissue pH sensor, an intracardiac pressure sensor, an intrathoracic pressure sensor, a positive end expiratory pressure sensor, a respiratory rate sensor, an intracranial pressure sensor, an intraocular pressure sensor, a respiratory flow sensor, an oxygen delivery sensor, a tissue $CO_2$ sensor, and a cardiac output sensor.

19. The device of claim 1, wherein the processor is in communication with one or more circulation enhancement devices.

20. The device of claim 19, wherein the circulation enhancement device is configured to generate a negative intrathoracic pressure within a patient.

* * * * *

UNITED STATES PATENT AND TRADEMARK OFFICE
CERTIFICATE OF CORRECTION

| | |
|---|---|
| PATENT NO. | : 10,835,175 B2 |
| APPLICATION NO. | : 15/927607 |
| DATED | : November 17, 2020 |
| INVENTOR(S) | : Keith G. Lurie |

Page 1 of 1

It is certified that error appears in the above-identified patent and that said Letters Patent is hereby corrected as shown below:

In the Claims

Column 15, Line 16-17, Claim 15, delete "further comprising further comprising" and insert
-- further comprising --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*